United States Patent [19]

Mack

[11] Patent Number: 4,913,954

[45] Date of Patent: Apr. 3, 1990

[54] DISPOSABLE PAD FOR ODOR PREVENTION IN CAT LITTER BOXES

[75] Inventor: Robert J. Mack, Aberdeen, N.J.

[73] Assignee: Colgate-Palmolive Company, New York, N.Y.

[21] Appl. No.: 113,092

[22] Filed: Oct. 26, 1987

[51] Int. Cl.$^4$ .............................................. B32B 7/02
[52] U.S. Cl. .................................... 428/213; 422/212; 422/224; 422/287
[58] Field of Search ............... 428/221, 280, 282, 284, 428/298, 326, 357, 402, 537, 913, 238, 239, 74, 65, 287, 213, 215, 212; 119/1

[56] References Cited

U.S. PATENT DOCUMENTS

| | | | |
|---|---|---|---|
| 4,140,225 | 2/1987 | Yanaton | 119/1 |
| 4,468,428 | 8/1984 | Early et al. | 428/221 |
| 4,494,482 | 1/1985 | Arnold | 119/1 |
| 4,517,919 | 5/1985 | Benjamin et al. | 119/1 |
| 4,774,907 | 10/1988 | Yanaton | 119/1 |

*Primary Examiner*—James J. Bell
*Attorney, Agent, or Firm*—Norman Blumenkopf; Murray M. Grill

[57] ABSTRACT

A disposable pad for odor prevention comprising a fluid impervious backing sheet, a top sheet and a pad sandwiched between the backing sheet and said top sheet, said pad being formed substantially of hydrophobic fibers so as to quickly disperse liquid waste for rapid evaporation.

3 Claims, 1 Drawing Sheet

DISPOSABLE PAD FOR ODOR PREVENTION IN CAT LITTER BOXES

BACKGROUND OF THE INVENTION

1. Field of the Invention

This invention relates to the class of animal husbandry, and, more particularly, to a disposable pad for use in odor control of a liquid waste from a cat litter box.

2. Description of the Prior Art

In the past, cat litter boxes have been provided with a filling of an absorbent material, such as sawdust, clay, earth or products generally known as cat litter. This material has been highly regarded and widely used and, recently, the convenient disposable of such material with the animal waste has been facilitated by employment of litter box liners, such as disclosed in U.S. Pat. No. 4,469,046.

In addition, U.S. patent application Ser. No. 06/573,958 discloses the use of an absorbent material, such as wood fluff, which is highly absorbent in a pad for litter boxes. This absorbent material easily receives the liquid waste and disperses the same throughout the pad, but inhibits rapid evaporation of the liquid animal waste, thus, prolonging and intensifying the odors about the litter box.

SUMMARY OF THE INVENTION

The present invention overcomes the disadvantages of absorbent pads used in conjunction with cat litter boxes.

In accordance with the concepts of the present invention, there is provided a pad for odor reduction for a cat litter box, which includes a backing sheet and a top sheet having a pad of hydrophobic fibers sandwiched between. The fibers may be treated with a surfactant to increase the spreading qualities of the pad for liquid animal waste to, thus, enhance evaporation.

DETAILED DESCRIPTION OF THE INVENTION

Figure 1:
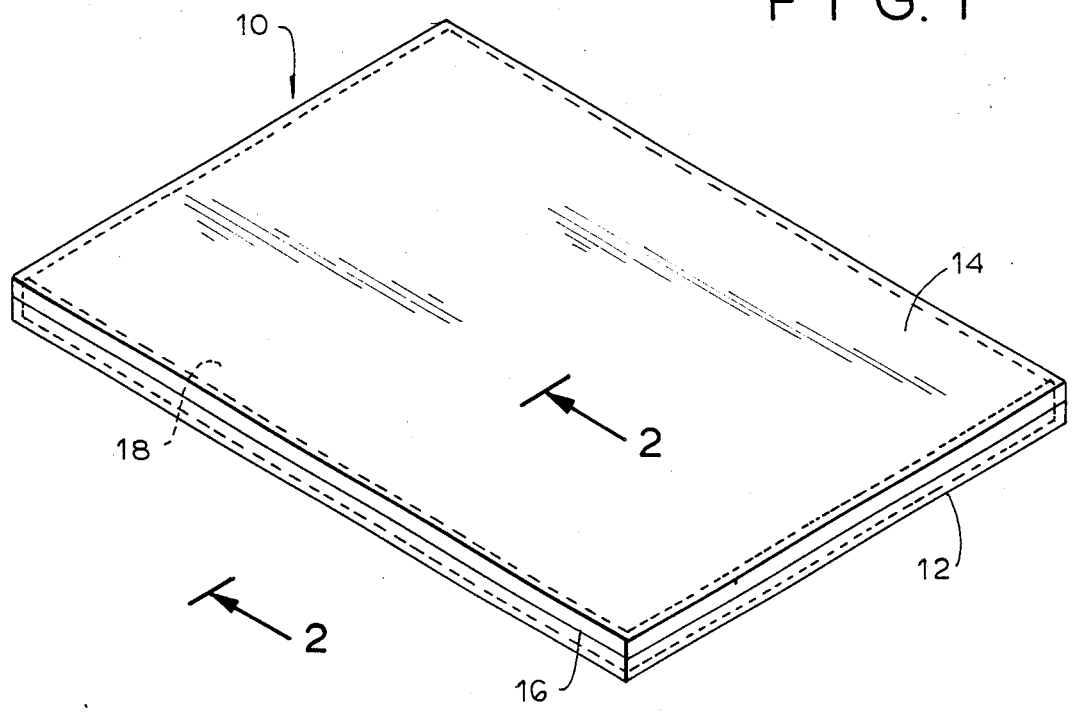
FIG. 1 is a perspective view of a pad constructed in accordance with the concept of the present invention; and, FIG. 2 is a sectional detail view in an enlarged scale, taken along the plane of line 2—2 in FIG. 1.
Figure 2:
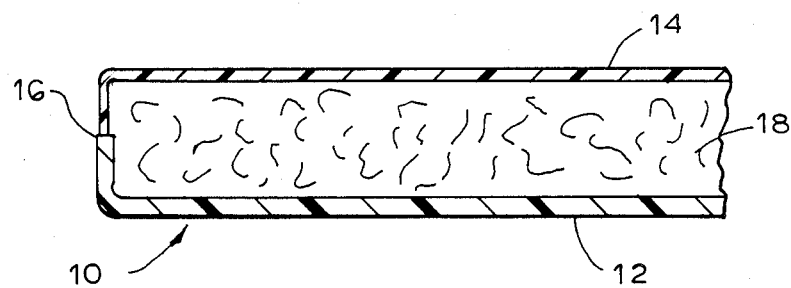

With continuing reference to the accompanying drawing, wherein like reference numerals designate similar parts, the pad constructed in accordance with the present invention is generally indicated at 10.

The pad 10 includes a backing sheet 12 of water impervious material, such as polyethylene or polypropylene film. A top sheet 14 preferably of non-woven hydrophobic fibers, such as polyethylene, polypropylene or polyester, is provided and, preferably, bonded to the backing sheet 12 along the peripheral edges 16 thereof.

Sandwiched between the backing sheet 12 and the top sheet 14 is a layer of hydrophobic fibers, such as polypropylene, polyethylene or polyester fibers. These fibers are substantially non-absorbent and receive the liquid waste in the fiber interspaces.

The hydrophobic fibers of layer 18 form a pad for reception of the liquid waste. Because of the non-absorbent quality thereof, evaporation is not held back by absorption by the fibers of any of the urine or the like.

As a modification, it is possible to use up to 35% of hydrophilic fibers, such as cellulose, i.e. wood fluff and the like, but it is to be expected that there will be some impedence by the absorbent qualities of the hydrophilic fibers.

It is to be noted that the pad may be washed and reused at least several times because the hydrophobic fibers will not clump and the pad will not become deformed and difficult to use.

It is possible to further enhance the distribution of liquid waste by coating the hydrophobic fibers of layer 18 with any suitable surfactant.

It is to be understood that the hydrophobic fibers of layer 18 are loosely compacted to provide voids for the waste liquid. Further, the layer 18 is generally many times, being at least two times, but may be four, ten, twenty, etc. times, thicker than said top layer 14.

What is claimed is:

1. A pad for cat litter boxes for facilitating evaporation of liquid waste comprising a fluid impervious backing sheet of material selected from the group consisting of polyethylene and polypropylene film, a top sheet of non-woven hydrophobic fibers selected from the group consisting of polyethylene, polypropylene and polyester, securd to said backing sheet, and a layer of hydrophobic fibers disposed between said top sheet and said backing sheet, the fibers of said layer being selected from the group consisting of polyethylene, polypropylene and polyester.

2. A pad according to claim 1, wherein said layer ranges between two and at least twenty times the thickness of said top sheet.

3. A pad according to claim 1, wherein said hydrophobic fibers of said layer are coated with a surfactant.

* * * * *